United States Patent [19]

Slininger et al.

[11] Patent Number: 5,552,315
[45] Date of Patent: Sep. 3, 1996

[54] BACTERIA FOR THE CONTROL OF FUSARIUM DRY ROT TO POTATOES

[75] Inventors: Patricia J. Slininger, Metamora; David A. Schisler, Morton; Rodney J. Bothast, East Peoria, all of Ill.

[73] Assignee: The United States of America as represented by the Secretary of Agriculture, Washington, D.C.

[21] Appl. No.: 295,583

[22] Filed: Aug. 25, 1994

Related U.S. Application Data

[60] Continuation-in-part of Ser. No. 199,409, Feb. 22, 1994, abandoned, which is a division of Ser. No. 68,872, May 28, 1993.

[51] Int. Cl.$^6$ .............................. C12N 1/00; C12N 1/20; C12Q 1/04; C12Q 1/18
[52] U.S. Cl. .................. 435/253.3; 435/32; 435/34; 435/252.1; 435/252.8; 435/267; 435/822; 435/874
[58] Field of Search .................................. 435/822, 874, 435/29, 4, 32, 34, 38, 252.4, 252.8, 267

[56] References Cited

U.S. PATENT DOCUMENTS

| | | | |
|---|---|---|---|
| 4,456,684 | 6/1984 | Weller et al. | 435/34 |
| 5,030,562 | 7/1991 | Elliott et al. | 435/29 |
| 5,163,991 | 11/1992 | Kennedy et al. | 71/79 |

OTHER PUBLICATIONS

Angela R. de la Cruz et al., "Biological Suppression of Potato Ring Rot by Fluorescent Pseudomonads", *Applied & Environmental Microbiology*, 58(6): 1986 (Jun. 1992).
P. D. Colyer, "Bacterization of Potatoes with *Pseduomonas putida* and Its Influence on Postharvest Soft Rot Diseases", *Plant Disease*, 68(8):703, (Aug. 1984).
Michael E. Wisniewski et al., "Biological Control of Post-harvest Diseases of Fruits and Vegetables: Recent Advances", *HortScience*, 27(2):94, (Feb. 1992).
T. J. Burr et al., "Increased Potato Yields by Treatment of Seedpieces with Specific Strains of *Pseudomonas fluorescens* and *P. putida*", *Disease Control & Pest Management*, 68, 1377 (Sep. 1978).

Milton N. Schroth et al., "Disease–Suppressive Soil and Root Colonizaing Bacteria", *Science*, 216:1376 (Jun. 1982).
D. A. Schisler et al., "Biological Control of Rhizoctonia Seedling Disease in Bedding Plant Nurseries with Thoughts Towards Commercial Development", Abstr. 191, Abstr. of Pres. of 1989 Annual Metg of the American Phytopathological Society, 79(10):1135, 1159, (1989).
D. A., Schisler et al., "Enrichment and Selection of Antagonists of *Fusarium sambuscinum* based on Efficacy and Performance in Liquid Culture", Abstr. A554, Abstr. of Pres. of 1992 APS/MSA Joint Mtg of The American Phytopathological Society, Portland, OR, Aug. 8–12, 1992.
D. J. Rhodes et al., "Selection of Pseudomonas Strains Which Inhibited Potato Tuber Rots Caused by *Erwinia carotovora* subsp. *atropeptica (Eca)* and *Fusarium sambucinum*", Abst., Abstr. 169, *Phytopathology*, 76(10), 1078.
P. J. Slininger et al., "Liquid Culture Growth Characteristics As Criteria for Selecting and Applying Bacterial ANtagonists of Potato Dry Rot", Abstract of Papers, 206th ACS National Meeting, Abstr. 100, (Aug. 22–27, 1993).
D. A. Schisler et al., "Selection and Performance of Bacterial Strains for Biologically Controlling Fusarium Dry Rot of Potatoes Incited by *Gibberella pulicaris*", *Plant Disease*, (Mar. 1994), pp. 251–255.
P. J. Slininger et al., "Two–dimensional Liquid Culture Focusing: A Method of Selecting Commercially Promising Microbial Isolates with Demonstrated Biological Control Capability", Proc. of Third International Workshop on Plant Growth–Promoting Rhizobacter, Adelaid, South Australia, (Mar. 7–11, 1994). pp. 29–32.

*Primary Examiner*—Esther M. Kepplinger
*Assistant Examiner*—Curtis E. Sherrer
*Attorney, Agent, or Firm*—M. Howard Silverstein; Curtis P. Ribando; John D. Fado

[57] ABSTRACT

Bacteria which will suppress fungus-induced potato disease under storage conditions have been screened and selected from soil samples. A method for isolating these antagonists, their use in controlling potato disease, and specific isolates which are inhibitory to potato dry rot disease under postharvest conditions constitute the essence of the invention. The subject biocontrol agents are considered to be economically-feasible alternatives to chemical agents currently in use for this purpose.

11 Claims, No Drawings

BACTERIA FOR THE CONTROL OF FUSARIUM DRY ROT TO POTATOES

CROSS-REFERENCE TO RELATED APPLICATIONS

This application is a continuation-in-part of Ser. No. 08/199,409, filed on Feb. 22, 1994, now abandoned which in turn is a division of Ser. No. 08/068,872, filed on May 28, 1993.

BACKGROUND OF THE INVENTION

1. Field of the Invention

The present invention relates to the biological control of fungal potato diseases. More particularly, this invention relates to the selection and use of bacterial isolates which are effective antagonists against fungal species responsible for potato dry rot and other potato diseases which occur in the field or in postharvest storage.

2. Description of the Art

The potato is the most important dicotyledonous source of human food, ranking as the fifth major food crop of the world. *Fusarium*-induced potato dry rot is an economically important problem of potatoes both in the field and in storage. Several species of the Fusaria induce this disease, however, *Gibberella pulicaris* (Fries) Sacc. (anamorph: *Fusarium sambucinum* Fuckel) is a major cause worldwide, especially in North America. *Fusarium* spp. can survive for years in field soil, but the primary inoculum is generally borne on seed tuber surfaces. The dry rot fungi infect potatoes via wounds in the periderm inflicted during harvesting or subsequent handling. In stored potatoes, dry rot develops most rapidly in high relative humidity (≧70%) and at 15°–20° C., but continues to advance at the coldest temperatures safe for potatoes. Although rots caused by *Fusarium* seldom reach epidemic proportions, the level of infected tubers in storage often reaches 60% or higher, with average losses estimated in the 10–20% range. In addition to destroying tissue, *F. sambucinum* can produce trichothecenes that have been implicated in mycotoxicoses of humans and animals.

The high value of the potato crop and the significant economic losses caused by potato dry rot have led to investigations of various methods to control the disease. Success has been attained by use of the fungicides, thiabendazole and 2-aminobutane, which are applied to tubers at harvest or at preplanting [S. F. Carnegie et al., *Ann Appl. Biol.* 116: 61–72 (1990); S. S. Leach, "Control of Postharvest *Fusarium* Tuber Dry Rot of White Potatoes," pages 1–7 In ARS-NE-55, U.S. Dep. Agric., Washington, D.C.]. However, strong concerns are being raised about the potential adverse impact of these chemicals on ground and surface water reservoirs and on the health of agricultural product workers and consumers. Also, thiabendazole-resistant strains of *F. sambucinum* have emerged in populations from severely dry-rotted tubers in North America and in Europe. Potato breeding programs have given increased attention to development of cultivars with resistance to *Fusarium*, but most of the reported cultivars produced by these programs are resistant to only one or two of several *Fusarium* strains [S. S. Leach et al., *Phytopathology* 71(6): 623–629 (1981)].

One alternative to chemical fungicides in controlling potato rot is the use of biological agents. Postharvest biological control systems of fruit have been actively investigated for the past decade. These include iturins as antifungal peptides in biological control of peach brown rot with *Bacillus subtilis* [C. G. Gueldner, et al., *Journal of Agricultural and Food Chemistry* 36:366–370 (1988)]; postharvest control of blue mold on apples using *Pseudomonas* spp. isolate L-22-64 or white yeast isolate F-43-31 [W. J. Janisiewicz, *Phytopathology* 77:481–485 (1987)]; control of gray mold of apple by *Cryptococcus laurentii* [R. G. Roberts, *Phytopathology* 80: 526–530 (1990)]; biocontrol of blue mold and gray mold on apples using an antagonistic mixture of *Pseudomonas* sp. and *Acremonium breve* [W. J. Janisiewicz, *Phytopathology* 78:194–198 (1988)]; control of gray mold and reduction in blue mold on apples and pears with an isolate of *Pseudomonas capacia* and pyrrolnitrin produced therefrom [W. J. Janisiewicz and J. Roitman, *Phytopathology* 78:1697–1700 (1988)]; postharvest control of brown rot in peaches and other stone fruit with the B-3 strain of *Bacillus subtills* [P. L. Pusey and C. L. Wilson, *Plant Disease* 68:753–756 (1984)]; P. L. Pusey et al., *Plant Disease* 72:622–626 (1988)] and U.S. Pat. No. 4,764,371 to Pusey et al.); antagonistic action of *Trichoderma pseudokoningii* against *Botrytis cinerea* Pers. which causes the dry eye rot disease of apple [A. Tronsmo and J. Raa, *Phytopathol. Z.* 89:216–220 (1977)] and postharvest control of brown rot and alternaria rot in cherries by isolates of *Bacillus subtilis* and *Enterobacter aerogenes* [R. S. Utkhede and P. L. Sholberg, *Canadian Journal of Microbiology* 963–967 (1986)]. A review of biological control of postharvest diseases of fruits and vegetables is given by Wisniewski et al. [*HortScience,* 27:94–98 (1992)].

Efforts have also been made to isolate bacterial agents for controlling diseases and weeds affecting yields of gramineous crops. In U.S. Pat. No. 4,456,684, Weller et al. disclose a method for screening *Pseudomonas fluorescens* strains which are effective in suppressing *Gaeumannomyces graminis* var. tritici (Ggt) in field-grown crops and turf grass. Elliott et al. have isolated non-fluorescent *Pseudomonas* bacteria useful in the selective control of downy brome in small grain crop fields (U.S. Pat. No. 5,030,562). Similarly, Kennedy et al. teach the screening for bacterial strains for controlling jointed goat grass, a weedy pest in small grain crops (U.S. Pat. No. 5,163,991).

Reports have been made in the literature regarding the application of *Pseudomonas* spp. as antagonists against organisms responsible for degradation of potatoes. Curiously enough, worldwide interest in these gram-negative bacteria was sparked by 1970s research in which strains of *P. fluorescens* and *putida*, applied to seed pieces, improved the growth of potatoes [T. J. Burr et al., *Phytopathology* 68: 1377–83 (1978)]. Later studies documented that fluorescent pseudomonads increased the yield of potato 5–33% [M. N. Schroth et al., Science 216: 1376–81 (1982)]. Colyer et al. report partial control of soft rot development in potato tubers by a *Pseudomonas putida* isolate antagonistic to soft-rotting *Erwinia* spp. [*Plant Disease,* 68:703–705 (1984)]. De La Cruz et al. disclose the isolation of three strains of fluorescent pseudomonads from potato underground stems antagonistic against 30 strains of the ring rot bacterium *Clavibacter michiganensis* subsp. *sepedonicus* [*Applied and Environmental Micro.,* 58:1986–91 (1992)]. Presently, there are no biocontrol systems for potato diseases in widespread commercial use.

SUMMARY OF THE INVENTION

We have now discovered a novel method for screening and selecting bacteria which will suppress (reduce the incidence or severity of) fungal-induced potato diseases under storage conditions. Applying this method to a variety of soil samples, we have isolated specific candidate antagonists which have demonstrated superior suppressive properties against *F. sambucinum* (*G. pulicaris*). The method comprises the following steps:

(a) cultivating putative bacterial antagonists of fungal species in the presence of potato periderm and under conditions suitable for propagation of the antagonists;

(b) selecting a community of the antagonists cultivated in (a) using a first competitive assay against the fungal species on a first wounded potato tuber material; and (c) selecting an antagonist from isolates of the community selected for in (b) using a second competitive assay against the fungal species on a second wounded potato tuber material.

In accordance with this discovery, it is an object of this invention to provide a method of screening for strains of microorganisms having the ability to proliferate in potato tuber material and having the property of inhibiting fungal species-induced potato diseases, and especially *Fusarium*-induced potato dry rot disease, under post-harvest conditions.

Another object of the invention is to provide specific strains of gram-negative bacteria which are antagonists against potato dry rot disease.

More particularly, it is an object of the invention to provide strains of bacteria which are economically-feasible alternatives to chemical agents currently in use for controlling dry rot disease in potatoes.

A further object of the invention is to offer the potato industry a method for the post-harvest control of dry rot in both market and seed potatoes.

Other objects and advantages of this invention will become readily apparent from the ensuing description.

Deposit of Biological Material

Five bacterial antagonists isolated by the screening and selection procedure described herein have been deposited under the terms of the Budapest Treaty on Feb. 22, 1993, in the U.S.D.A., Agricultural Research Service Patent Culture Collection in Peoria, Ill., and were assigned Accession Numbers NRRL B-21048, NRRL B-21049, NRRL B-21050, NRRL B-21051, and NRRL B-21053. Five additional strains were deposited in the Agricultural Research Service Patent Culture Collection under the terms of the Budapest Treaty on May 26, 1993, and were assigned Accession Numbers NRRL B-21101, NRRL B-21102, NRRL B-21103, NRRL B-21104, and NRRL B-21105. Eight additional strains were deposited under the terms of the Budapest Treaty on Aug. 30, 1993, in the Agricultural Research Service Culture Collection, and were assigned Accession Numbers NRRL B-21128, NRRL B-21129, NRRL B-21132, NRRL B-21133, NRRL B-21134, NRRL B-21135, NRRL B-21136 and NRRL B-21137.

DETAILED DESCRIPTION OF THE INVENTION

For purposes of this invention it is understood that the use of the term "*Fusarium*" is intended to include both the sexual (teleomorphic) stage of this organism and also the asexual (anamorphic) stage, which are also referred to as the perfect and imperfect fungal stages, respectively. For example, the anamorphic stage of *Gibberella pulicaris* (Fries) Sacc. is known as *Fusarium sambucinum*. Fuckel). *Fusarium*-induced potato dry rot is a disease caused when a potato wound becomes inoculated with conidia produced by the imperfect form of this fungus.

The expression "suppressive microbial community" as used in the ensuing description refers to one or more populations of organisms which coexist in the same microenvironment and which collectively exhibit some degree of control over fungal species-induced potato disease. It is understood that some strains which exist in such a community may be highly effective in controlling potato disease, whereas others within the community may have no such effect. Thus, a soil sample which supports a suppressive microbial community, may contain a multitude of strains which individually exhibit the full range of natural biological control over fungal species.

The expression "superior suppressive" used herein in conjunction with the terms "microbial community", "microbe", "bacterium", "isolate", "strain", or the like is in reference to a population selected at any point during the course of the screening procedure described herein; wherein the population exhibits a degree of inhibition of fungal-induced potato disease (i.e. proliferation of an agent responsible for the disease) exceeding, at a statistically significant level, that of an untreated control.

A detailed outline for the screening and selection of bacterial antagonists in accordance with the invention includes the following steps:

(a) obtaining a soil sample from a field recently cropped to potatoes and with a low incidence of a potato disease-causing fungal species or a low incidence of potato disease;

(b) combining a minor amount of the soil sample from (a) with a major amount of sterilized soil and a sterilized potato periderm amendment;

(c) cultivating the mixture from (b) under conditions suitable for propagation of putative fungal antagonists originally present in the soil sample;

(d) inoculating the cultivated mixture from (c) with conidia of the fungal species and incubating the mixture under conditions suitable for propagation of the fungal species;

(e) bioassaying wounded potato tubers with the incubated mixture from (d) and selecting for a suppressive soil community based on a low level of diseased tissue in the bioassayed potato tubers;

(f) obtaining microbial isolates from a suppressive soil community obtained in (e);

(g) subjecting a candidate microbial isolate from (f) to a competitive assay against the fungal species on a potato tuber wound; and (h) selecting for an isolate from (g) which is efficacious in inhibiting growth of the fungal species.

Although the bacterial strains of the invention may be relatively widespread throughout the environment, the method described herein for screening and selecting the organisms targets soils in which potatoes have been cropped and from which harvested potatoes exhibit a relatively low incidence of the potato disease to be controlled. The premise for this choice of soils is that the low level of disease can be attributable to antagonistic organisms with a high level of probability.

Soil samples from candidate sites are subjected to a first competitive assay for identifying suppressive microbial communities. In preparation for this assay, it is considered important to subject the soil sample to conditions which provide cultivation conditions which favor the propagation of antagonistic organisms and which suppress the proliferation of competing organisms. For this purpose, a minor amount of the soil sample is combined with a major amount of sterilized receiver soil. Another function of the sterilized receiver soil is to provide an environment chemically and physically similar to, yet independent of, the suppressive soil samples. Thus, variation in antagonism shown by individual test soils after antagonist propagation is attributable to biological differences and not to, for example, antagonistic soil chemistries. This is because the bulk of the soil in all assays is the common receiver soil. A sandy loam or sandy clay loam soil is typical for cropping potatoes and ideally the receiver soil is of a soil type similar to that of the sample and is sterilized by gamma irradiation. This sterilization method tends to be less destructive of soil physical and chemical properties than gaseous sterilants, steam sterilization or dry heat sterilization, all of which could also be used. Alternatively, soil samples may be analyzed for mineral and organic matter contents, pH and the like by techniques known in the art; and a similar, receiver soil could then be reconstructed.

In the preferred embodiment of the invention, the sterilized soil is amended with sterilized potato periderm (skin) for the purpose of providing nutrients which would likely favor the buildup of microbes that could utilize these nutrients for growth. The presence of the periderm amendment would thereby enhance the probability of selecting for a microbial community which normally associates with the potato surface in the field. The actual ratios of the soil sample, periderm and sterilized soil are not particularly critical. The objective in selecting the proportions is simply to minimize the population of unwanted, potentially competing organisms and to maximize the compatible environment for the suppressive community. In the assay illustrated in the Examples below, a soil sample:periderm:sterilized soil weight ratio of 5:2:93 was used. The moisture level of the soil medium is adjusted as necessary so as to be conducive to proliferation of the microbes in the periderm-enriched background as well as to proliferation of the subsequently added fungal inoculum. Likewise, an incubation temperature in the range of about 5°–25° C., preferably about 10°–20° C., and especially about 15° C., is selected to promote cultivation of the suppressive organisms.

Incubation of the medium is continued for at least about 3 days, and preferably for 7–10 days with periodic shaking. During this period, a sufficient population of soil microbes should be present to give a valid indication of suppressiveness in the subsequent stages of the screen. At this point, the medium is inoculated with the target fungal species, such as by spraying with a highly concentrated aqueous conidial suspension. The effective ranges of inoculum concentration and particle size are those which optimize the selection of suppressive communities and minimize the selection of nonsuppressive communities. The concentration of fungal inoculum must be high enough so that sufficient inoculum pressure is placed on the suppressive microbes to insure that microbes having little or no suppressive activity are not selected. Conversely, the concentration of inoculum must be low enough so that the fungus does not overwhelm the suppressive activity of the microbial community. As a rule, it is desired to achieve a final inoculum concentration of at least about $1 \times 10^4$ conidia per gram soil. The conidia are thoroughly mixed with the soil medium and then incubated at a temperature and for a time normally suitable for propagation of the fungus. Typically, the conditions will be on the order of about 5°–25° C., preferably 10°–20° C., and more preferably about 15° C., for a period of about 2 days.

The competitive assays are conducted on wounds of potato tuber material. In the first such assay, wounded potato tuber material (e.g., wounded potatoes) are simultaneously challenged with the incubated soil comprising a combination of the soil sample microflora and the fungal pathogen. The simultaneous challenge of the potato tissue with the pathogen and the prospective antagonist(s) is important to the reliability of this screening procedure. Artificially-induced wounds are contacted with the soil, and the tubers are incubated in darkness under conditions conducive to dry rot. The extent of dry rot after a period of about 3–4 weeks in comparison to a control group provides an indication of the effectiveness of the microbial community in the test soil to inhibit the disease. The level of infection is most easily measured by the amount of necrotic tuber tissue. Based on observance of minimal or no tuber disease, superior suppressive communities can be selected. However, it is also possible to blindly isolate primary colonists from a wound early in the assay and then pursue only those early communities which originated from wounds showing minimal disease at the 3–4 week harvest.

The strategy for isolating bacterial antagonists of fungal pathogens from the superior suppressive communities is to sample from disease-free zones of tuber tissue in the vicinity of a treated wound. Typically, a tissue sample would be excised and macerated in an aqueous medium, serially diluted in buffer, and plated on a selective medium under conditions to promote bacterial growth. Standard techniques for executing these steps are described in Eklund and Landkford, *Laboratory Manual for General Microbiology*, Prentice-Hall, Inc., (1967), pp. 21–27. Generally, plating conditions will be in the temperature range of 20°–27° C. for a period of 2–5 days.

To maximize the number of efficacious strains isolated, it is desired to use media which simulate the nutritional conditions to which soil organisms have adapted. Such media would contain low concentrations of complex nitrogen and carbon sources and would have a neutral to slightly acidic pH. Examples of general media which propagate a broad number of bacteria include nutrient broth yeast agar (NYB), nutrient agar and the like. Preferred selective media include one-quarter strength potato dextrose agar (PDA/4)+ 0.05 g/L cycloheximide and one-tenth strength tryptic soy broth agar+cycloheximide (TSBA/10). Another suitable selection medium includes acidified "YME" agar containing 3.0 g/L yeast extract, 3.0 g/L malt extract, 5.0 g/L peptone (Type III) and 0.1 g/L chloramphenicol, acidified with 1M HCl to pH 3.7 after autoclaving. Bacteria and yeasts were preferentially isolated on TSBA/10 and YME respectively. Other selection media such as King's medium 'B' (KMB) amended with the antibiotics novobiocin, penicillin and cycloheximide could also be used. The latter has been demonstrated by others to be useful for identifying pseudomonads.

Isolates from the previous step may be treated by conventional microbiological techniques, such as restreaking, to insure purity and stability. Isolates are maintained by storing as slant cultures at low temperatures (about 5° C.), by storing in a aqueous solution of glycerol at −80° C., or by lyophilizing and storing at −10° C.

Candidate antagonists are identified through a systematic survey of isolates from each morphologically distinct colony. This is accomplished by means of a second competitive assay on wounded potato tuber material. The wounded tissue is coinoculated with the selected isolate and fungal conidia, and incubated as described above for the suppressive soil assay. After a period sufficient to allow for the onset of dry rot, the tubers are evaluated for the extent of fungal colonization as described above in the discussion of the suppressive soil assay. From these results, superior suppressive strains are selected.

As illustrated in the Examples below, the aforementioned screening and selection procedures for bacterial antagonists of fungal pathogens appear to favor the selection of gram-negative bacteria, such as species of *Pseudomonas, Enterobacter* and *Pantoea*. Notwithstanding, any other organism which is selected by the inventive process and is inhibitory to potato dry rot is considered to be fully within the scope of the invention.

Optimal conditions for the cultivation of antagonists isolated by the method of the invention will, of course, depend upon the particular isolate. However, by virtue of the conditions applied in the selection process and general requirements of most microorganisms, a person of ordinary skill in the art would be able to determine essential nutrients and conditions.

The antagonists would typically be grown in aerobic liquid cultures on media which contain sources of carbon, nitrogen, and inorganic salts assimilable by the microorganism and supportive of efficient cell growth. Preferred carbon sources are hexoses such as glucose, but other assimilable sources include glycerol, amino acids, xylose, etc. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

For most organisms contemplated to be within the scope of the invention, cell growth can be achieved at temperatures between 1° and 40° C., with the preferred temperature being in the range of 15°–30° C. The pH of the nutrient medium can vary between 4 and 9, but the preferred operating range is 6–8. Ordinarily, maximal cell yield is obtained in 20–72 hours after inoculation.

Prime candidate antagonists for commercial development are those which are readily propagated in liquid culture under conventional conditions using standard nutrients. We have recently discovered that biocontrol efficacy and liquid culture growth kinetics are not necessarily positively correlated. A method referred to as "two-dimensional liquid culture focusing" for selecting commercially promising microbial isolates with demonstrated biological control capability has been described by the applicants in *Proceedings of the Third International Workshop on Plant Growth-Promoting Rhizobacteria*, pp. 29–32 (Mar. 7–11, 1994), herein incorporated by reference. By application of that method, it was determined that the six isolates described herein having the highest commercial application are B-21050, B-21128, B-21133, B-21134, B-21132, and B-21102.

The antagonists of the invention can be applied by any conventional method to the surfaces of potato tuber material, to include without limitation whole potato tubers, potato tuber parts, or seed tubers. For example, they can be applied as an aqueous spray or dip, as a wettable powder, or as a dust. Formulations designed for these modes of application will usually include a suitable liquid or solid carrier together with other adjuvants, such as wetting agents, sticking agents and the like. Starch, polysaccharides, sodium alginate, cellulose, etc. are often used in such formulations as carriers and sticking agents.

The expressions "an effective amount" and "a suppressive amount" are used herein in reference to that quantity of antagonist treatment which is necessary to obtain a reduction in the level of disease relative to that occurring in an untreated control under suitable conditions of treatment as described herein. The actual rate of application of a liquid formulation will usually vary from a minimum of about $1\times10^3$ to about $1\times10^{10}$ viable cells/ml and preferably from about $1\times10^6$ to about $1\times10^9$ viable cells/ml. Most of the strains described in the examples, below, would be optimally effective at application rates in the range of about $1\times10^6$ to $1\times10^9$ viable cells/ml, assuming a mode of application which would achieve substantially uniform contact of at least about 90% of the potato surface. If the antagonists are applied as a solid formulation, the rate of application should be controlled to result in a comparable number of viable cells per unit area of potato surface as obtained by the aforementioned rates of liquid treatment.

It is envisioned that the temperatures at which the antagonists are effective would range from about 5° C. to about 30° C. The preferred temperature range is 10°–25° C., and the optimal range is considered to be 12°–20° C. Therefore, the antagonists can theoretically be applied at any time during the harvest, grading, or shipping process, or during the early stages of storage. Of course, potato tubers are susceptible to infection any time a wound occurs and the fungal disease agent is present. Therefore, the longer the delay between the tuber wounding and the treatment with the antagonist organism, the greater the chance the pathogen will successfully infect the tuber. Though we have demonstrated that delays of 4 h between wounding and treatment did not significantly affect antagonist performance, it is anticipated that longer delays may decrease the effectiveness of the microbial treatment depending on methods of cell formulation and application.

It would be appreciated by the person in the art that organisms selected against a particular fungal species by the aforementioned procedure may incidentally be inhibitory toward other fungal and bacterial species responsible for tuber diseases such as soft rot, ring rot, black and silver scurf, and the like. Additionally, it would be appreciated that the screening method of the invention could be readily tailored for the specific selection of antagonists against these other species.

The following examples are intended only to further illustrate the invention and are not intended to limit the scope of the invention which is defined by the claims.

EXAMPLE 1

Assay for suppressive microbial communities against *F. sambucinum* (causative agent of potato dry rot disease)

Soil samples obtained primarily from fields cropped to potatoes and with a low incidence of *F. sambucinum* were collected from 27 different sites in Wisconsin and 2 sites in Illinois as shown in Table I. Soils were sieved through 2 mm screens and stored for not more than 5 months at 4° C. in loosely closed plastic bags. Slightly moist field soil samples (approx. soil water potential=–0.5 megapascal), powdered, heat-sterilized Russett Burbank potato periderm, and gamma irradiation-sterilized (5 megarads minimum) sandy clay loam field soil (pH 6.8, 1.3% organic matter) were then combined in a weight ratio of 5:2:93, respectively. Four randomly selected field soils were also used to construct mixtures without potato periderm to determine if enrichment influenced soil suppressiveness. The water potential of each mixture was adjusted to approximately −0.1 megapascal and the mixtures incubated in plastic bags for 1 week at 15° C. with periodic shaking. Highly concentrated aqueous suspensions of seven day old conidia of *F. sambucinum* isolate R-6380, were then added by misting conidial solutions over each soil mixture to obtain a final concentration of $1\times10^6$ conidia per gram soil (dry weight equivalent). Bags containing inoculated soil mixtures were shaken thoroughly and incubated for 2 days at 15° C.

Tubers of potato cultivar Russet Burbank were used for assays of soil suppressiveness. Tubers were wounded at the stem and apical ends using a board containing 4 blunted nails (4 mm long, 2 mm diameter) positioned at each corner of a 1×1 cm square. Aqueous pastes of each soil were then immediately applied to each end of the wounded tubers. Controls consisted of wounded potatoes inoculated with a paste of sterile field soil and uninoculated wounded potatoes. Trays were enclosed in large plastic bags and incubated in darkness at 15° C. for 4 weeks.

Three days after tuber inoculation, two wounds from one tuber per treatment were excavated using sterile toothpicks and the cell matter obtained streaked onto one-tenth strength tryptic soy broth agar+cycloheximide (TSBA/10) and acidified "YME" agar containing 3.0 g/L yeast extract, 3.0 g/L malt extract, 5.0 g/L peptone (Type III) and 0.1 g/L chloramphenicol, acidified with 1M HCl to pH 3.7 after autoclaving. Bacteria and yeasts were preferentially isolated on TSBA/10 and YME respectively. Samples were plated in the event that some primary colonists active in suppressing dry rot could be more readily recovered soon after wounding rather than after determining the extent of dry rot at assay harvest 4 weeks after tuber inoculation. Plates were stored in plastic bags for 4 weeks at 4° C. until the data from the suppressive soil assay were analyzed.

In three of four soils assayed, potato periderm decreased the amount of disease compared to the same soil without periderm amendment. For these paired soil treatments, diseased tissue measurements averaged 0.52 cm for soils with periderm compared to 0.66 cm for soils without periderm (not significantly different, paired-t test, P=0.54). For all soils, the range of treatment means for diseased tissue was 0.18 cm to 0.94 cm. All of the 18 most suppressive organisms ultimately isolated came from soils that had been amended with periderm (29 soils). None came from unamended soils (4 soils).

Isolation of microorganisms

Immediately after harvesting the suppressive soil assay, data were analyzed to determine superior suppressive soils. The five most suppressive soils included 4 soils with periderm amendment and 1 without. (Note: The 18 most inhibitory strains eventually selected were from soils with the periderm amendment.) Microorganisms were then isolated from two disease-free wedges chosen from tubers harvested from each selected treatment. A 2 mm square piece of tissue was cut from around each wound of a selected wedge, the fresh weight determined, and the tissue pieces macerated with a sterile scalpel. The macerate was then diluted in 0.1% water agar, agitated for two minutes using a vortex mixer and serial dilutions prepared in pH 7.2, 0.004% phosphate buffer with 0.019% $MgCl_2$ ($PO_4$ buffer; Aid-Pack USA, Gloucester, Mass.). Dilutions were dispensed into plates of acidified YME+chloramphenicol, TSBA/10+cycloheximide and one-quarter strength potato dextrose agar (PDA/4)+0.05 g/L cycloheximide. After incubation for 3 days at 27° C., colony counts of bacteria were made and several isolates of each morphologically distinct colony from each medium were isolated in pure cultures. For the five superior treatments from the suppressive soil assay, additional putative antagonists were isolated from the streak plates made from tissues excavated from potato wounds three days after initiating the assay. Isolates were streaked for purity and stored at −80° C. in 10% glycerol until needed.

Assay of efficacy of bacterial strains against *F. sambucinum* R-6380

Four initial single replication assays using whole potato tubers were performed to evaluate the efficacy of strains in controlling *F. sambucinum*. Only those strains which completely or virtually completely controlled disease were selected for further testing. A total of 353 strains were tested, roughly 90 strains per assay. Just prior to use, slightly turbid microbial suspensions (absorbance of 0.170 at 620 nm; corresponding to a cell count of approx. $1\times10^8$ cells/ml) in PO4 buffer were prepared from 18-h-old cultures grown on TSBA/5. Russett Burbank tubers, obtained from commercial sources, were prepared as described above except that 4 individual wounds were made at equal distances around the circumference of tubers. Conidia of *F. sambucinum* R-6380 (NRRL 13708; $1\times10^6$ conidia/ml, prepared as described previously) and a microbial suspension were then combined 1:1 and thoroughly mixed in a microtiter dish and 5 μl was inoculated into one wound per microbial treatment. Controls consisted of tubers which were inoculated with $PO_4$ buffer or the macroconidial suspensions only. Tubers were placed in trays and incubated as previously described. Tubers were harvested after three weeks and the extent of disease evaluated.

Of 353 strains tested in the initial single replication assays, 44 provided sufficient control to warrant further testing. These 44 superior strains were then evaluated in a first replicated experiment which included *Pseudomonas fluorescens* strain 2–79 for comparison of the test treatments with an agent having known biological control capabilities. Fifteen of the 44 strains assayed significantly inhibited disease development compared to the control inoculated with conidia of *F. sambucinum* R-6380 (P=0.05 or 0.01). The *P. fluorescens* strain 2–79 failed to significantly inhibit the disease. A second replicated experiment was conducted using the best 18 strains from the first replicated experiment. All 18 bacterial isolates tested significantly inhibited disease development (P=0.01), as did control strain 2–79. None of the bacterial treatments significantly differed from the wound only or wound+heat-killed conidia controls (P=0.05). Limited browning of tissues around the wounds of controls was not due to the presence of *F. sambucinum*, but due to suberization of tissues adjacent to some wounds. The results from the first and second replicated experiment are presented in Table II, below, under the headings "1A" and "1B". The data are reported in terms of the extent of disease which is represented by the sum of the length and depth of the necrotic tissue incited by the pathogen as measured from a wound site.

Seventeen of the 18 effective bacterial strains (S series) were recovered from day 28 dilution plates made after terminating the suppressive soil assay while only 1 effective strain (P series) was recovered from plates inoculated with plant matter excavated from wounds 3 days after initiating the assay. Effective strains were recovered primarily from two of the five soils with the highest level of *Fusarium* dry rot suppressiveness. A higher percentage of strains recovered from PDA/4 and TSA/10 were effective than those recovered on YME medium (5.8%, 8.9% and 1.7%, respectively).

The 10 most effective isolates in terms of disease inhibition as determined by the aforementioned assay were all gram-negative bacteria. These were deposited under the terms of the Budapest Treaty on either Feb. 22, 1993, or on May 26, 1993, in the U.S.D.A. Agricultural Research Service Patent Culture Collection in Peoria, Ill., and were assigned the accession numbers indicated below in Table III.

The taxonomic characteristics of these isolates are as follows:

B21053 *Pseudomonas* sp. Gram-negative, oxidase-positive, motile rods. Aerobic, negative for levan production, positive for fluorescent pigments, gelatin liquefaction, arginine dihydrolase, lecithinase, lipase, and denitrification.

B21049 *Pseudomonas* sp. Gram-negative, oxidase-positive motile rods. Aerobic, negative for fluorescent pigments, lecithinase, and lipase and positive for levan production, gelatin liquefaction, and denitrification.

B21051 *Pseudomonas* sp. Gram-negative, oxidase-positive motile rods. Aerobic, negative for fluorescent pigments, lecithinase, and lipase and positive for levan production, gelatin liquefaction, and denitrification.

B21048 *Pantoea* (*Enterobacter*) *agglomerans*. Gram-negative, motile rods. Facultatively anaerobic, catalase positive, oxidase-negative, reduce nitrate to nitrite, yellow pigment, lack of gas from glucose and negative reactions for arginine dihydrolase and lysine and ornithine decarboxylases.

B21050 *Enterobacter cloacae*. Gram-negative, motile rods. Facultatively anaerobic, catalase positive, oxidase-negative, reduce nitrate to nitrite, negative lysine, positive arginine and ornithine, negative indole, and positive KCN and sorbitol reactions.

B21105 *Pseudomonas* sp. Gram negative, oxidase-positive motile rods. Aerobic, negative for fluorescent pigments, lecithinase and lipase and positive for levan production, gelatin liquefaction and denitrification.

B21102 *Pseudomonas* sp. Gram-negative, oxidase-positive motile rods. Aerobic, negative for lipase and denitrification and positive for fluorescent pigments, levan production, lecithinase, gelatin liquefaction.

B21104 *Pantoea* (*Enterobacter*) sp. Gram-negative, motile rods. Facultatively anaerobic, oxidase negative, yellow pigment, lack of gas from glucose, positive for Voges-Proskauer, negative reactions for arginine dihydrolase and lysine and ornithine decarboxylases, negative for sorbitol.

B21103 *Enterobacter* sp. Gram-negative, motile rods. Facultatively anaerobic, oxidase negative, gas from glucose, positive for Voges-Proskauer, positive for arginine dihydrolase and ornithine decarboxylase and negative for lysine decarboxylase, positive for sorbitol.

B21101 *Enterobacter* sp. Gram-negative, motile rods. Facultatively anaerobic, oxidase-negative, gas from glucose, positive for Voges-Proskauer, positive for arginine dihydrolase and ornithine decarboxylase and negative for lysine decarboxylase, positive for sorbitol.

The remaining isolates were also all gram-negative bacteria. These were deposited under the terms of the Budapest Treaty in the U.S.D.A. Agricultural Research Service Patent Culture Collection in Peoria, Ill., on Aug. 30, 1993, and were assigned the accessions numbers indicated below in Table IV. The taxonomic characteristics of these isolates are as follows:

B21128 *Pseudomonas* sp. Gram negative, oxidase positive, motile rods. Aerobic, negative for denitrification and positive for levan production, fluorescent pigments, gelatin liquefaction, arginine dihydrolase, lecithinase, and lipase.

B 21129 *Pseudomonas* sp. Gram negative, oxidase positive, motile rods. Aerobic, variable for levan production, negative for fluorescent pigments, lipase, and denitrification and positive for gelatin liquefaction, arginine dihydrolase and lecithinase.

B 21132 *Enterobacter* sp. Gram negative, oxidase negative, motile rods. Facultatively anaerobic, negative for lysine decarboxylase and positive for gas from glucose, Voges-Proskauer, arginine dihydrolase, ornithine decarboxylase and sorbitol.

B-21133 *Pseudomonas* sp. Gram negative, oxidase positive, motile rods. Aerobic, negative for levan production and denitrification, and positive for fluorescent pigments, gelatin liquefaction, arginine dihydrolase, lecithinase and lipase.

B-21134 *Pseudomonas* sp. Gram negative, oxidase positive, motile rods. Aerobic, negative for levan production and denitrification, and positive for fluorescent pigments, gelatin liquefaction, arginine dihydrolase, lecithinase and lipase.

B-21135 *Pseudomonas* sp. Gram negative, oxidase positive, motile rods. Aerobic, negative for levan production and denitrification, and positive for fluorescent pigments, gelatin liquefaction, arginine dihydrolase, lecithinase and lipase.

B-21136 *Pseudomonas corrugata*. Gram negative, oxidase positive, motile rods. Aerobic, negative for fluorescent pigments, lecithinase, and lipase and positive for levan production, gelatin liquefaction, arginine dihydrolase and denitrification.

B-21137 *Pseudomonas* sp. Gram negative, oxidase positive, motile rods. Aerobic, negative for levan production and denitrification and positive for fluorescent pigments, gelatin liquefaction, arginine dihydrolase, lecithinase and lipase.

EXAMPLE 2

The effect of cell concentration on antagonist efficacy

The assay for efficacy of bacterial strains against *F. sambucinum* R-6380 described in Example 1 was repeated at three cell concentration treatment levels. For Example 2A, the cell count was the same as in Example 1, namely $1 \times 10^8$ cells/ml (corresponding to an absorbance of 0.170 at 620 nm). For Example 2B, the cell count was $1 \times 10^7$ cells/ml (corresponding to an absorbance of 0.017 at 620 nm). For Example 2C, the cell count was $1 \times 10^6$ cells/ml (corresponding to an absorbance of 0.002 at 620 nm). All other conditions of the assay were identical to those described in Example 1. The results are reported in Table II. In general, it was found that the efficacy is concentration dependent. Though, $1 \times 10^7$ cells/ml of P22:1:Y:05, $1 \times 10^7$ cells/ml of S09:3:T:12, $1 \times 10^6$ cells/ml of S09:3:Y:08, and $1 \times 10^7$ cells/ml of S09:4:P:08 appeared to provide equivalent protection to $1 \times 10^8$ cells/ml in each case.

EXAMPLE 3

Assay of efficacy of bacterial strains against TBZ-sensitive and TBZ-resistant strains of *F. sambucinum*

The antagonists reported in Table II were assayed for efficacy against the thiabenzadole-sensitive (TBZ-sensitive)

*F. sambucinum* strain RN-5 (Ex. 3A) and the thiabenzadole-resistant (TBZ-resistant) *F. sambucinum* strain RN-1 (Ex. 3B) by the same procedure described in Example 1 for assay against strain R-6380. The results are reported in Table II. It is noteworthy that many of the isolates, particularly those which were considered to be the most inhibitory, were effective against the TBZ-resistant strain of *F. sambucinum*.

TABLE I

Soil Sample Origins

| Ship # | Samp # | Soil location general[a] | Soil location specific | Potato variety or crop grown in previous cropping year |
|---|---|---|---|---|
| 1 | 1 | Hancock | r12.bk2 | hybrid |
| 1 | 2 | Hancock | r29.bk7 | Superior |
| 1 | 3 | Hancock | r12.bk6 | hybrid |
| 1 | 4[b] | Hancock | r27.bk12 | hybrid |
| 1 | 5 | Hancock | r1.bk1 | R. Burbank |
| 1 | 6 | Hancock | r14.bk11 | hybrid |
| 2 | 7 | Rhinelander | S E corner | Norland |
| 2 | 8 | Rhinelander | N C W side | Red Pontiac |
| 2 | 9[b,c] | Rhinelander | UW, N E corner | Norland |
| 2 | 10 | Rhinelander | N W corner | Red Pontiac |
| 2 | 11[b,d] | Rhinelander | N C E side | Norland |
| 2 | 12 | Rhinelander | S C W side | Red Pontiac |
| 2 | 13 | Rhinelander | S W corner | Norland |
| 2 | 14 | Rhinelander | S C E side | Red Pontiac |
| 3 | 15 | Sturgeon bay | corn field Cnt | corn |
| 3 | 16 | Sturgeon bay | corn field N | corn |
| 3 | 17 | Sturgeon bay | corn field S | corn |
| 3 | 18 | Sturgeon bay | field 9 N end | experimental |

TABLE I-continued

Soil Sample Origins

| Ship # | Samp # | Soil location general[a] | Soil location specific | Potato variety or crop grown in previous cropping year |
|---|---|---|---|---|
| 3 | 19[b] | Sturgeon bay | field 9 S end | experimental |
| 3 | 20 | Sturgeon bay | field 9 Cnt | experimental |
| 3 | 21 | Sturgeon bay | field 2 S end | experimental |
| 3 | 22[b,e] | Sturgeon bay | field 0 W end | experimental |
| 3 | 23 | Sturgeon bay | field 0 S end | experimental |
| 3 | 24 | Sturgeon bay | field 0 Cnt | experimental |
| 3 | 25 | Sturgeon bay | backfield E end | experimental |
| 3 | 26 | Sturgeon bay | backfield Cnt | experimental |
| 3 | 27 | Sturgeon bay | backfield W end | experimental |
| 4 | 28 | Peoria | garden 1 | experimental |
| 4 | 29 | Peoria | garden 2 | experimental |

[a]Hancock = University of Wisconsin Agricultural Experiment Station, Hancock, WI
Rhinelander = University of Wisconsin Lelah Starks Potato Breeding Farm, University of Wisconsin Agricultural Experiment Station, Rhinelander, WI
Sturgeon Bay = University of Wisconsin Agricultural Experiment Station, Sturgeon Bay, WI
Peoria = National Center for Agricultural Utilization Research, Peoria, IL
[b]Yielded suppressive soil communities.
[c]Yielded isolates S09:3:P:06, S09:3:T:14, S09:3:P:14, S09:3:P:12, S09:4:T:04, S09:4:T:10, S09:3:Y:08 and S09:4:P:08.
[d]Yielded isolates S11:3:T:04, S11:3:T:06, S11:1:P:08, S11:1:P:12, S11:1:P:14, S11:1:T06, and S:11:3:P:02.
[e]Yielded isolates P22:1:Y:05, S22:1:T:04, and S22:1:T:10.

TABLE II

Antagonist Control of *F. sambucinum*[a,b]

| | Example: | | | | | | |
|---|---|---|---|---|---|---|---|
| | 1A | 1B | 2A | 2B | 2C | 3A | 3B |
| | | | | Challenge: | | | |
| | R-6380 | R-6380 | R-6380 | R-6380 | R-6380 | RN-1 | RN-5 |
| | | | | Cell count: | | | |
| Isolate | $1 \times 10^8$ | $1 \times 10^8$ | $1 \times 10^8$ | $1 \times 10^7$ | $1 \times 10^6$ | $1 \times 10^8$ | $1 \times 10^8$ |
| 1 P22:1:Y:05 (TOP 5)[c] | 0.5** | 0.0** | 13.0** | 3.3** | 28.8 | 1.3** | 12.5** |
| 2 S09:3:P:14 (TOP 10)[d] | 0.5** | 0.8** | 3.5** | 12.8* | 23.8 | 0.4** | 2.4** |
| 3 S09:3:P:06 (TOP 5) | 0.0** | 0.3** | 3.0** | 6.5** | 26.0 | 1.1** | 2.1** |
| 4 S09:3:T:12 (TOP 10) | 0.8** | 0.5** | 6.5** | 4.3** | 19.5 | 7.9** | 11.4* |
| 5 S09:3:T:14 (TOP 5) | 1.0* | 0.3** | 2.8** | 5.0** | 11.8* | 0.6** | 9.4** |
| 6 S09:3:Y:08 | 1.5 | 1.0** | 10.5** | 3.5** | 4.8** | 4.1** | 10.5* |
| 7 S09:4:P:08 | 1.0* | 0.5** | 5.3** | 4.3** | 25.3 | 10.5** | 8.1* |
| 8 S09:4:T:04 (TOP 10) | 1.8 | 0.5** | 2.5** | 3.8** | 6.3** | 3.0** | 3.6** |
| 9 S09:4:T:10 (TOP 10) | 1.0* | 1.0** | 2.3** | 9.8** | 18.8 | 7.3** | 6.0** |
| 10 S11:1:P:08 | 0.8** | 1.3** | 4.0** | 11.3 | 13.3 | 12.5** | 4.9** |
| 11 S11:1:P:12 | 0.8** | 0.5** | 5.8** | 7.5** | 17.3 | 22.3* | 16.3 |
| 12 S11:1:P:14 | 2.8 | 1.0** | 8.8** | 8.3** | 16.3 | 17.3** | 8.8** |
| 13 S11:1:T:06 | 1.3 | 0.3** | 10.8* | 19.3 | 23.3 | 17.0** | 5.9** |
| 14 S11:3:P:02 | 1.0* | 0.8** | 11.8* | 15.8 | 30.0 | 3.6** | 1.5** |
| 15 S11:3:T:04 (TOP 5) | 1.0* | 0.0** | 3.8** | 15.0 | 8.3** | 3.0** | 1.8** |
| 16 S11:3:T:06 (TOP 5) | 0.7** | 0.8** | 4.5** | 17.5 | 22.0 | 1.5** | 5.1** |
| 17 S22:1:T:04 (TOP 10) | 1.0* | 0.5** | 3.0** | 6.8** | 28.8 | 3.0** | 4.0** |
| 18 S22:1:T:10 | 0.5** | 0.5** | 4.8** | 10.8* | 20.3 | 4.0** | 6.8** |
| 2-79 | 2.8 | 0.8** | 2.8** | 7.0** | 5.8** | 11.0** | 4.3** |
| Control F6380 | 6.1 | 21.2 | 27.9 | 27.9 | 27.9 | — | — |
| Control RN-1 (TBZ RES) | — | — | — | — | — | 39.2 | — |
| Control RN-5 (TBZ SEN) | — | — | — | — | — | — | 25.0 |

[a]Data represents extent of diseased tissue on tuber cross-section expressed as the sum of the width and depth of the necrotic tissue in mm.
[b]*, ** = Significantly different than control at P = 0.05, 0.01, respectively.
[c]"TOP 5" indicates isolate is one of the five most efficacious isolates found in the survey described in the Examples.
[d]"TOP 10" indicates isolate in one of the ten most efficacious isolates found in the survey.

TABLE III

Superior Isolates

| Isolate | | | |
|---|---|---|---|
| No. | Designation | Taxonomic description | Accession No. |
| 1 | P22:1:Y:05 | Pseudomonas sp. | NRRL B-21053 |
| 3 | S09:3:P:06 | Pseudomonas sp. | NRRL B-21049 |
| 5 | S09:3:T:14 | Pseudomonas sp. | NRRL B-21051 |
| 15 | S11:3:T:04 | Pantoea[a] agglomerans | NRRL B-21048 |
| 16 | S11:3:T:06 | Enterobacter cloacae | NRRL B-21050 |
| 2 | S09:3:P:14 | Pseudomonas sp. | NRRL B-21105 |
| 17 | S22:1:T:04 | Pseudomonas sp. | NRRL B-21102 |
| 4 | S09:3:T:12 | Pantoea[a] sp. | NRRL B-21104 |
| 8 | S09:4:T:04 | Enterobacter sp. | NRRL B-21103 |
| 9 | S09:4:T:10 | Enterobacter sp. | NRRL B-21101 |

[a] Formerly Enterobacter.

TABLE IV

Remaining Isolates

| Isolate | | | |
|---|---|---|---|
| No. | Designation | Taxonomic description | Accession No. |
| 6 | S09:3:Y:08 | Pseudomonas sp. | NRRL B-21128 |
| 7 | S09:4:P:08 | Pseudomonas sp. | NRRL B-21129 |
| 10 | S11:1:P:08 | Enterobactor sp. | NRRL B-21132 |
| 11 | S11:1:P:12 | Pseudomonas sp. | NRRL B-21133 |
| 12 | S11:1:P:14 | Pseudomonas sp. | NRRL B-21134 |
| 13 | S11:1:T:06 | Pseudomonas sp. | NRRL B-21135 |
| 14 | S11:3:P:02 | Pseudomanas corrugata | NRRL B-21136 |
| 18 | S22:1:T:10 | Pseudomonas sp. | NRRL B-21137 |

We claim:

1. A biologically pure culture of a bacterial antagonist of *Fusarium* selected from the group consisting of *Pantoea agglomerans* NRRL B-21048, *Pseudomonas* sp. NRRL B-21049, *Enterobacter cloacae* NRRL B-21050, *Pseudomonas* sp. NRRL B-21051, *Pseudomonas sp.* NRRL B-21053, *Enterobacter* sp. NRRL B-21101, *Pseudomonas sp.* NRRL B-21102, *Enterobacter* sp. NRRL B-21103, *Pantoea* sp. NRRL B-21104, *Pseudomonas* sp. NRRL B-21105, *Pseudomonas* sp. NRRL B-21128, *Pseudomonas* sp. NRRL B-21129, *Enterobacter* sp. NRRL B-21132, *Pseudomonas sp.* NRRL B-21133, *Pseudomonas* sp. NRRL B-21134, *Pseudomonas* sp. NRRL B-21135, *Pseudomonas corrugata* NRRL B-21136 and *Pseudomonas* sp. NRRL B-21137.

2. A bacterial antagonist of claim 1, wherein said antagonist is *Pantoea agglomerans* NRRL B-21048.

3. A bacterial antagonist of claim 1, wherein said antagonist is *Pseudomonas* sp. NRRL B-21049.

4. A bacterial antagonist of claim 1, wherein said antagonist is *Enterobacter cloacae* NRRL B-21050.

5. A bacterial antagonist of claim 1, wherein said antagonist is *Pseudomonas* sp. NRRL B-21051.

6. A bacterial antagonist of claim 1, wherein said antagonist is *Pseudomonas* sp. NRRL B-21053.

7. The bacterial antagonist of claim 1, wherein said antagonist is *Pseudomonas* sp. NRRL B-21102.

8. The bacterial antagonist of claim 1, wherein said antagonist is *Pseudomonas* sp. NRRL B-21128.

9. The bacterial antagonist of claim 1, wherein said antagonist is *Enterobacter* sp. NRRL B-21132.

10. The bacterial antagonist of claim 1, wherein said antagonist is *Pseudomonas* sp. NRRL B-21133.

11. The bacterial antagonist of claim 1, wherein said antagonist is *Pseudomonas* sp. NRRL B-21134.

* * * * *